US009770420B2

(12) United States Patent
Haag et al.

(10) Patent No.: US 9,770,420 B2
(45) Date of Patent: Sep. 26, 2017

(54) METHOD FOR PRODUCING A POLYGLYCEROL NANOGEL FOR THE ENCAPSULATION AND RELEASE OF BIOLOGICALLY ACTIVE SUBSTANCES

(71) Applicant: FREIE UNIVERSITÄT BERLIN, Berlin (DE)

(72) Inventors: Rainer Haag, Berlin (DE); Dirk Steinhilber, Berlin (DE); Wolfgang Friess, Iffeldorf (DE); Sarah Küchler, München (DE); Madeleine Witting, München (DE)

(73) Assignee: FREIE UNIVERSITÄT BERLIN, Berlin (DE)

(*) Notice: Subject to any disclaimer, the term of this patent is extended or adjusted under 35 U.S.C. 154(b) by 53 days.

(21) Appl. No.: 14/426,713

(22) PCT Filed: Sep. 5, 2013

(86) PCT No.: PCT/EP2013/068343
§ 371 (c)(1),
(2) Date: Mar. 6, 2015

(87) PCT Pub. No.: WO2014/037429
PCT Pub. Date: Mar. 13, 2014

(65) Prior Publication Data
US 2015/0283094 A1 Oct. 8, 2015

(30) Foreign Application Priority Data

Sep. 7, 2012 (DE) .......................... 10 2012 108 345

(51) Int. Cl.
*A61K 9/51* (2006.01)
*A61K 38/38* (2006.01)
*C07K 16/00* (2006.01)
*B01J 13/00* (2006.01)
*A61K 9/06* (2006.01)
*A61K 38/50* (2006.01)

(52) U.S. Cl.
CPC .............. *A61K 9/5146* (2013.01); *A61K 9/06* (2013.01); *A61K 9/5192* (2013.01); *A61K 38/385* (2013.01); *A61K 38/50* (2013.01); *B01J 13/0065* (2013.01); *C07K 16/00* (2013.01); *C12Y 302/01017* (2013.01); *C12Y 305/01001* (2013.01)

(58) Field of Classification Search
CPC ........ A61K 38/385; A61K 38/50; A61K 9/06; A61K 9/5146; A61K 9/5192; B01J 13/0065
See application file for complete search history.

(56) References Cited

U.S. PATENT DOCUMENTS 9,138,383 B1* 9/2015 Stansbury ............... A61K 6/083
2009/0011420 A1 1/2009 Barron et al.
2009/0117070 A1 5/2009 Daniloff et al.

FOREIGN PATENT DOCUMENTS

DE         102 11 664 A1    10/2003
DE    10 2008 030 992 A1     1/2010
EP         2 138 527 A1     12/2009
EP            2138527   *   12/2009 ............. C08G 83/00

OTHER PUBLICATIONS

Sisson et al. (Polyglycerol nanogels: higly funcitonl scaffolds for biomedical applicaitons, Soft Matter, 2010, 6 4968-4975).*
http://www.chem.ucla.edu/~bacher/Specialtopics/rotavap.html 2010.*
Pattison, David I., Aldwin Suryo Rahmanto, and Michael J. Davies. "Photo-oxidation of proteins." Photochemical & Photobiological Sciences 11.1 (2012): 38-53.
C. Bertozzi et al. Angew. Chem. "Bioorthogonal Chemistry: Fishing for Selectivity in a Sea of Functionality" Int. Ed. Engl. 2009, 48, 6974-6998.
"Prinzipien der Chemie" (Chemical Principles) by Dickerson et al. (2. ed 1988, Walter de Gruyter Verlag, Berlin, New York) in chapter 5-1 p. 187.
Sharpless et al. (K. B. Sharpless et al. "Click Chemistry: Diverse Chemical Function from a Few Good Reactions" Angew. Chem. Int. Ed. Engl. 2001, 40, 2004-2021).
A. L. Sisson, I. Papp, K. Landfester, R. Haag, "Functional Nanoparticles from Dendritic Precursors: Hierarchical Assembly in Miniemulsion" Macromolecules 2009, 42, 556-559.
A. L. Sisson, D. Steinhilber, T. Rossow, P. Welker, K. Licha, R. Haag, "Biocompatible Functionalized Polyglycerol Microgels with Cell Penetrating Properties" Ang. Chem. Int. Ed. 2009, 48, 7540-7545.
D. Steinhilber, A. L. Sisson, D. Mangoldt, P. Welker, K. Licha, R. Haag, "Synthesis, Reductive Cleavage, and Cellular Interaction Studies of Biodegradable, Polyglycerol Nanogels" Adv. Funct. Mater. 2010, 20, 4133-4138.

(Continued)

Primary Examiner — Anna Falkowitz
(74) Attorney, Agent, or Firm — Maschoff Brennan

(57) ABSTRACT

A method for producing a polyglycerol nanogel is disclosed, the method comprising the following steps: Mixing an aqueous solution of first polyglycerol macromonomers, which are modified with a first reactive group, with an aqueous solution of second polyglycerol macromonomers, which are modified with a second reactive group, wherein the first reactive group and the second reactive group can react with each other forming a chemical bond; transferring the mixture into an organic non-solvent; and precipitation of a polyglycerol nanogel consisting of first polyglycerol macromonomers and second polyglycerol macromonomers which are covalently bound to each other. According to an aspect of the invention, the method is characterized in that the organic non-solvent is miscible with water and in that the method is carried out without adding surface-active substances.

12 Claims, 8 Drawing Sheets

(56) References Cited

OTHER PUBLICATIONS

H. Zhou, D. Steinhilber, H. Schlaad, A. L. Sisson, R. Haag, "Glycerol based polyether-nanogels with tunable properties via acid-catalyzed epoxide-opening in miniemulsion" React. Funct, Polym. 2011, 71, 356-361.

Adeishvili, K. "Glycerol-Induced Aggregation of the Oligomeric L-Asparaginase II from *E. coli* Monitored with ATR-FTIR", International Journal of Molecular Sciences, vol. 2, Issue 2, Jun. 28, 2001, pp. 109-120.

Calder'on et al., "Dendritic Polyglycerols for Biomedical Applications", Advanced Materials, vol. 22, Issue 2, Jan. 12, 2010, pp. 190-218.

Dernedde et al., "Dendritic polyglycerol sulfates as multivalent inhibitors of inflammation", Proceedings of the National Academy of Sciences, vol. 107, Issue 46, Nov. 16, 2010, pp. 19679-19684.

Hawe et al., "Forced Degradation of Therapeutic Proteins", Journal of Pharmaceutical Sciences, vol. 101, Issue 3, Mar. 2012.

Hendrickson et al., "Design of Multiresponsive Hydrogel Particles and Assemblies", Advanced Functional Materials, vol. 20, Issue 11, Jun. 9, 2010, pp. 1697-1712.

Hong et al., "Analysis and Optimization of Copper-Catalyzed Azide-Alkyne Cycloaddition for Bioconjugation", Angewandte Chemie International Edition in English, vol. 48, Issue 52, Dec. 21, 2009, pp. 9879-9883.

Jiskoot et al., "Protein Instability and Immunogenicity: Roadblocks to Clinical Application of Injectable Protein Delivery Systems for Sustained Release", Journal of Pharmaceutical Sciences, vol. 101, Issue 3, Mar. 2012, pp. 946-954.

Kabanov et al., "Nanogels as Pharmaceutical Carriers: Finite Networks of Infinite Capabilities", Angewandte Chemie International Edition, vol. 48, Issue 30, 2009, 5418-5429.

Kainthan et al., "In vivo biological evaluation of high molecular weight hyperbranched polyglycerols", Biomaterials, vol. 28, Issue 32, Nov. 2007, pp. 4779-4787.

Kazemi et al., "Regioselective Azidolysis of Epoxides Catalyzed with LiBF4", Synthetic Communications: An International Journal for Rapid Communication of Synthetic Organic Chemistry, vol. 33, Issue 6, 2003, pp. 999-1004.

Khandare et al., "Multifunctional dendritic polymers in nanomedicine: opportunities and challenges", Chemical Society Reviews, vol. 41, Issue 7, Apr. 7, 2012, pp. 2824-2848.

Khandare et al., "Structure-biocompatibility relationship of dendritic polyglycerol derivatives", Biomaterials, vol. 31, Issue 15, May 2010, pp. 4268-4277.

Malkoch et al., "Synthesis of well-defined hydrogel networks using Click chemistry", Chemical Communications, Issue 26, 2006, pp. 2774-2776.

Mashburn et al., "Tumor Inhibitory Effect of L-Asparaginase", Biochemical and Biophysical Research Communications, vol. 12, Issue 1, Jul. 10,1963, pp. 50-55.

Ofek et al., "In vivo delivery of small interfering RNA to tumors and their vasculature by novel dendritic nanocarriers", Federation of American Societies for Experimental Biology, vol. 24, Issue 9, Sep. 2010, pp. 3122-3134.

Quadir et al., "Biofunctional nanosystems based on dendritic polymers", Journal of Controlled Release, vol. 161, Issue 2, Jul. 20, 2012, pp. 484-495.

Richards, F. M., "Protein stability: still an unsolved problem", Cellular and Molecular Life Sciences, vol. 53, Oct. 1997, pp. 790-802.

Roberts et al., "The Antitumor Activity of *Escherichia coli* L-Asparaginase[1]", Cancer Research, vol. 26, Oct. 1966, pp. 2213-2217.

Roller et al., "High-loading polyglycerol supported reagents for Mitsunobu- andacylation-reactions and other useful polyglycerol derivatives", Molecular Diversity, vol. 9, Issue 4, Nov. 2005, pp. 305-316.

Rossow et al., "Controlled Synthesis of Cell-Laden Microgels by Radical-Free Gelation in Droplet Microfluidics", Journal of the American Chemical Society, vol. 134, Issue 10, Mar. 14, 2012, pp. 4983-4989.

Schubert et al., "Nanoprecipitation and nanoformulation of polymers: from history to powerful possibilities beyond poly (lactic acid)", Soft Matter, vol. 7, Issue 5, 2011, pp. 1581-1588.

Siegers et al., "Self-Assembled Monolayers of Dendritic Polyglycerol Derivatives on Gold That Resist the Adsorption of Proteins", Chemistry—A European Journal, vol. 10, Issue 11, Jun. 7, 2004, pp. 2831 -2838.

Steinhilber et al., "Surfactant free preparation of biodegradable dendritic polyglycerol nanogels by inverse nanoprecipitation for encapsulation and release of pharmaceutical biomacromolecules", Journal of Controlled Release, vol. 169, Issue 3, Aug. 10, 2013, pp. 289-295.

Takemoto et al., "Accelerated Polymer-Polymer Click Conjugation by Freeze-Thaw Treatment", Bioconjugate Chemistry, vol. 23, Issue 8, Aug. 15, 2012, pp. 1503-1506.

Va'zque z-Rey et al., "Aggregates in Monoclonal Antibody Manufacturing Processes", Biotechnology and Bioengineering, vol. 108, Issue 7, Jul. 2011.

Wang et al., "Immunogenicity of protein aggregates—Concerns and realities", International Journal of Pharmaceutics, vol. 431, Issue 1-2, Jul. 15, 2012, pp. 1-11.

Weinhart et al., "Linear Poly(methyl glycerol) and Linear Polyglycerol as Potent Protein and Cell Resistant Alternatives to Poly(ethylene glycol)", Chemistry—An Asian Journal, vol. 5, Issue 9, Sep. 3, 2010, pp. 1992-2000.

Weinhart et al., "Synthesis of Dendritic Polyglycerol Anions and Their Efficiency Toward L-Selectin Inhibition", Biomacromolecules, vol. 12, Issue 7, May 20, 2011, pp. 2502-2511.

Wilms et al., "Hyperbranched Polyglycerols: From the Controlled Synthesis of Biocompatible Polyether Polyols to Multipurpose Applications", Accounts of Chemical Research, vol. 43, Issue 1, Jan. 2010, pp. 129-141.

Wu et al., "Evaluating proteins release from, and their interactions with, thermosensitive poly (N-isopropylacrylamide) hydrogels", Journal of Controlled Release, vol. 102, Issue 2, Feb. 2, 2005, pp. 361-372.

Zhang et al., "Facile Engineering of Biocompatible Materials with pH-Modulated Degradability", Advanced Materials, vol. 23, Issue 27, Jul. 19, 2011, pp. 3035-3040.

Dickerson et al., "Prinzipien der Chemie" 2. ed 1988 Walter de Gruyter Verlag, Berlin, New York, chapter 5-1 p. 187.

\* cited by examiner

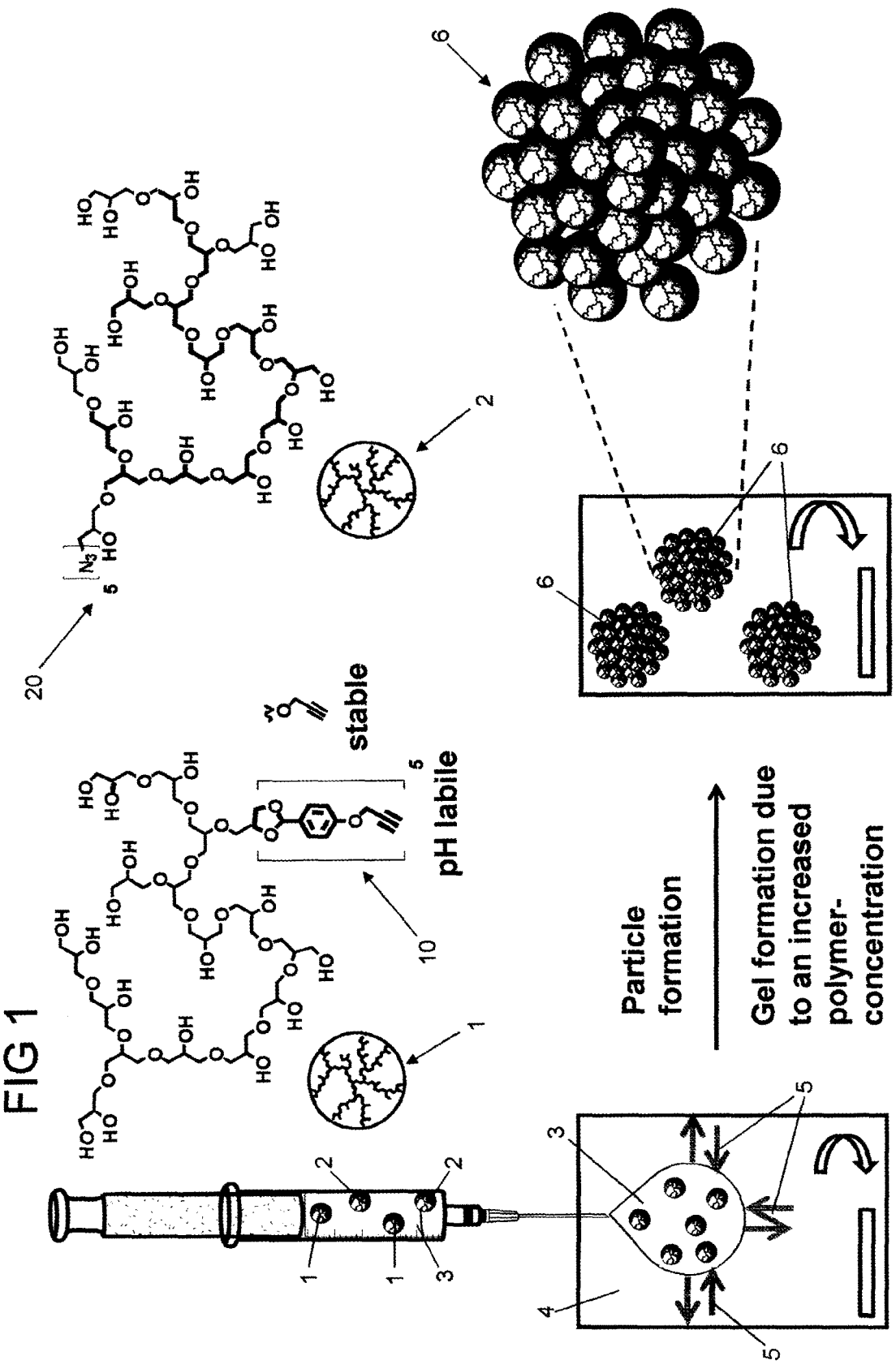

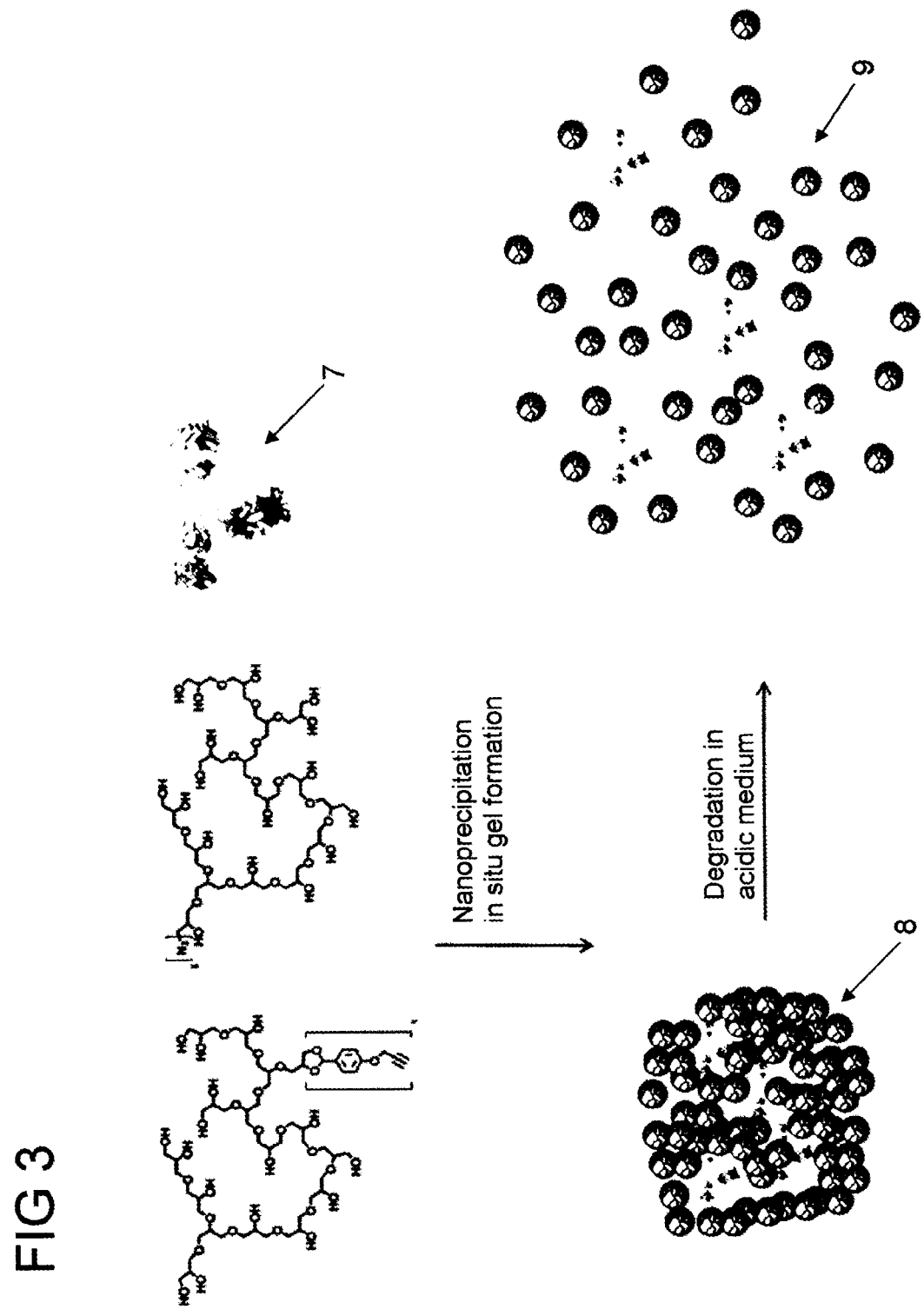

METHOD FOR PRODUCING A POLYGLYCEROL NANOGEL FOR THE ENCAPSULATION AND RELEASE OF BIOLOGICALLY ACTIVE SUBSTANCES

CROSS-REFERENCE TO A RELATED APPLICATION

This application is a national phase patent application of International patent application PCT/EP 2013/068343, filed on Sep. 5, 2013, which claims priority of German patent application 10 2012 108 345.2, filed on Sep. 7, 2012.

BACKGROUND

The present invention relates to a method for producing a polyglycerol nanogel.

Various methods for producing polyglycerol nanoparticles or polyglycerol nanogels are known from prior art (A. L. Sisson, I. Papp, K. Landfester, R. Haag, *Macromolecules* 2009, 42, 556-559;
  A. L. Sisson, D. Steinhilber, T. Rossow, P. Welker, K. Licha, R. Haag, *Ang. Chem. Int. Ed.*2009, 48, 7540-7545; D. Steinhilber, A. L. Sisson, D. Mangoldt, P. Welker, K. Licha, R. Haag, *Adv. Funct. Mater.* 2010, 20, 4133-4138; H. Zhou, D. Steinhilber, H. Schlaad, A. L. Sisson, R. Haag, *React. Funct, Polym.* 2011, 71, 356-361).

Also, EP 2 138 527 A1, for example, specifies a method for producing polyglycerol nanoparticles. According to this prior art method, mini or micro emulsions are formed in order to produce nanoparticles. In the method, it is always worked using a surface-active substance. Moreover, at various stages of the method an ultrasound treatment takes place. Also, the reaction temperatures are sometimes quite high. Under conditions that harsh, it is not possible to encapsulate substances that are chemically or physically sensitive to temperature, interfacial effects, ultrasound and extreme pH values, such as proteins, for instance, in the thus-formed polyglycerol nanogels while maintaining the activity.

From US 2009/0011420 A1 polymer nanogels are known which are formed by means of radical cross-linking Such a radical cross-linking is incompatible with an embedding of labile biomolecules in such a nanogel; the radicals persistently damage the labile biomolecules and, moreover, can inactivate them (Pattison, David I., Aldwin Suryo Rahmanto, and Michael J. Davies. "Photo-oxidation of proteins." *Photochemical & Photobiological Sciences* 11.1 (2012): 38-53.). Hence, the nanogels specified in that US patent application are not suited for the embedding of labile biomolecules, but instead for the electrophoretic separation of DNA molecules after the formation of the nanogels has taken place.

From DE 10 2008 030 992 A1 polyglycerol compounds are known which consist of a purely hydrophobic nucleus, which practically excludes the encapsulation of hydrophilic substances. Furthermore, basically only a low load efficiency with hydrophilic substances is to be expected due to the encapsulation in the aqueous phase. Thus, in said patent application no suitable method with which labile biomolecules can effectively be embedded in a polyglycerol compound is specified.

SUMMARY

The object underlying the present invention is to specify a novel producing method for a polyglycerol nanogel in which labile substances such as, for instance, therapeutic enzymes or proteins can be embedded in the nanogel during the formation of the nanogel while maintaining the activity.

This object is achieved with a method having the features explained in the following. In this method, first an aqueous solution of first polyglycerol macromonomers is mixed with an aqueous solution of second polyglycerol macromonomers. The first polyglycerol macromonomers are modified with a first reactive group and the second polyglycerol macromonomers are modified with a second reactive group. The first reactive group and the second reactive group can react with each other forming a chemical (covalent) bond. Such a reaction only takes place, however, when the concentration of the two macromonomers is sufficiently high. At a low concentration of the macromonomers, there is no reaction yet. Thereafter, the mixture of the first polyglycerol macromonomers and the second polyglycerol macromonomers is transferred to an organic non-solvent or an organic liquid. Thereby, the concentration of the macromonomers rises abruptly, as they do not dissolve in the non-solvent. Now it comes to a nanoprecipitation of a polyglycerol nanogel consisting of the first polyglycerol macromonomers and the second polyglycerol macromonomers, wherein the first macromonomers are covalently bound to the second macromonomers to form the nanogel. The covalent bond between the first polyglycerol macromonomers and the second polyglycerol macromonomers is here formed by a reaction of the first reactive group with the second reactive group, which only takes place spontaneously as a consequence of transferring the mixture into the organic non-solvent.

The method claimed according to an aspect of the invention is characterized in that the organic non-solvent or the organic liquid is miscible with water and that the method can be carried out entirely without adding surface-active substances. In other words, no surfactants or amphiphilic substances forming association colloids and reducing the interfacial tension are necessary for the chemical reaction (that is, the formation of the covalent bond between the first macromolecules and the second macromolecules) and the nanoparticle formation accompanying it. In particular, by not using surface-active substances such as surfactants, for instance, it is possible to precipitate proteins such as, for instance, therapeutic enzymes or other biologically active substances together with the macromonomers to form a polyglycerol nanogel. This is not possible with the methods known from prior art, as here the harsh conditions (particularly due to harsh ultrasound treatment and the presence of surface-active substances) regularly lead to a denaturation of proteins or an influencing of other active substances.

Surprisingly, however, the inventors were able to show that the presence of surface-active substances is not necessary when working in an organic non-solvent that is miscible with water. For when the mixture of first polyglycerol macromonomers and second polyglycerol macromonomers is transferred into the organic non-solvent, there is a diffusion of water from individual droplets of water containing the macromonomers into the surrounding non-solvent. Thereby, the concentration of the macromonomers in the aqueous phase rises, whereby a critical threshold concentration is exceeded. Thereby, the reaction between first polyglycerol macromonomers and second polyglycerol macromonomers is initiated.

Suitable non-solvents or organic liquids are, for example, polar organic liquids that are miscible with water but do not dissolve polyglycerol. Acetone and acetonitrile are especially suitable.

In particular, no surfactant is formed in the claimed reaction. The reaction products are rather purely hydrophilic structures without amphiphilic and surface-active properties. In case of a formation of surfactants, it could be expected that after a degradation of the formed nanogels due to spontaneous micelle formations, nanoparticulate structures were produced or persisted, which would be detectable, for example, with dynamic light scattering methods (DLS). As the inventors were able to show, however, no micellar structures at all are detectable after a nanogel degradation.

In an embodiment, the reactive groups in each case are bioorthogonal structures, whereby, according to the definition, chemical groups are specified which merely interact or react amongst each other but in no case interact with native biochemical processes or react with native molecules. A corresponding in-depth and detailed description of such bioorthogonal structures has been published by C. Bertozzi et al. (C. Bertozzi et al. Angew. Chem. Int. Ed. Engl. 2009, 48, 6974-6998).

In an embodiment, the nanoprecipitation method claimed here, moreover, can do without ultrasound treatment. Hence, the method can in a variant explicitly be carried out without ultrasound treatment. This allows for altogether very mild reaction conditions, by which the enzymes, other proteins or other active substances are not affected.

However, even without the additional use of enzymes, other proteins or other active substances, this method is excellently suited for producing polyglycerol nanogels on account of its particularly simple execution. In this context, it is pointed out that the term "nanogel" is presently used as equivalent to "nanoparticle", as this has prevailed in technical terminology.

In contrast to the methods known from prior art, particularly in contrast to the method specified in EP 2 138 527 A1,
(1) surface-active substances are not necessary for the reaction according to the presently claimed method,
(2) no ultrasound treatment is necessary for the particle production.

Surfactants and particularly the ultrasound treatment are methods which can significantly damage labile substances such as proteins/peptides, for instance, whereby a loss of activity can occur. Due to the mechanical stress of an ultrasound treatment, aggregates can form within a very short period of time, which, apart from a loss of function, can also be accompanied by an increase in immunogenicity. The method specified here is substantially gentler and, for the first time, makes possible the efficient and safe encapsulation of labile, hydrophilic substances.

In an embodiment, the presently claimed method makes use of a spontaneous concentration gradient in the aqueous phase, which automatically sets in due to a water diffusion out of the aqueous phase into the organic phase when the method is carried out. That is to say, the method takes place spontaneously in an embodiment. More specifically, the precipitation of the polyglycerol nanogel after transferring the mixture into the organic non-solvent takes place spontaneously in an embodiment. Such a spontaneous reaction is basically known to a person skilled in the art. Thus, a spontaneous reaction is defined in "Prinzipien der Chemie" (Chemical Principles) by Dickerson et al. (2. ed 1988, Walter de Gruyter Verlag, Berlin, N.Y.) in chapter 5-1 on page 187 as a chemical reaction which, given enough time, will take place by itself.

By an active merging of the two polyglycerol macromonomer solutions in the non-solvent by an operator, hence, the spontaneous precipitation and cross-linking of the nanogel is initiated in an embodiment. Thus, in this case, there is a double spontaneity with regard to the nanoparticle formation and the chemical cross-linking.

In an embodiment of the method, one works with a very low starting concentration of the macromonomers employed as starting materials. For, in this manner, it is ensured that the chemical reaction between the first polyglycerol macromonomers and the second polyglycerol macromonomers does not yet start in the aqueous phase, but instead is only initiated by increasing the concentration of the macromonomers. Hence, in an embodiment, the first macromonomers are present in a first concentration and the second macromonomers are present in a second concentration, wherein the first and the second concentration lie in the range of 0.1 to 30 mg/ml, independently of one another. A suited concentration range is 0.2 to 25 mg/ml, particularly 0.5 to 20 mg/ml, particularly 1 to 15 mg/ml, particularly 2 to 12 mg/ml and very particularly 3 to 10 mg/ml. The first concentration and the second concentration can here be the same or be different.

By choosing the concentration of the macromonomers, the size of the nanogel obtained can be adjusted. In this way, it could be shown that the diameter of the nanogel formed can be varied in a range of approximately 50 nm to approximately 1.000 nm depending on the concentration of the macromonomers. Here, particularly nanogels with a diameter (measured in acetone and determined by means of dynamic light scattering) of 100 to 600 nm, particularly 200 to 500 nm and very particularly of 300 to 400 nm are suitable variants.

In an alternative embodiment of the method, the polyglycerol nanogel is transferred into an aqueous phase after precipitation. This leads to the penetration of water into the nanogel, whereby the formed polyglycerol nanogel swells. This can be observed in an increase of the diameter of the nanogel. A nanogel thus swollen can in an especially suited manner be used as carrier substance for proteins and other active substances.

As already indicated several times, the method is in an embodiment executed in such a way that the precipitation of the nanogel is carried out in the presence of a labile substance, particularly of a peptide, a protein, an enzyme, a nucleic acid and/or a hormone. Other biologically active substances are equally conceivable as potential precipitation partners. As a consequence of the precipitation of the nanogel in the presence of such a substance, this substance is embedded inside of the nanogel. Polyglycerols are well known to show low interactions with proteins, whereby matrix-induced protein denaturation can be prevented. The use of branched polyglycerols creates a close-meshed nanogel network, in which the proteins are stably encapsulated by impeded diffusion. As long as the nanogel remains intact, the protein or the other active substance also remains inside of the nanogel.

In a further embodiment of the method, the first polyglycerol macromonomers and/or the second polyglycerol macromonomers have a pH-labile group. This pH-labile group is also contained in the formed nanogel after the reaction of the first reactive group of the first macromonomers. The pH-labile group can now be used to dissolve the structure of the formed nanogel depending on the pH value. In this manner, a biodegradable polyglycerol nanogel is therefore provided. When the pH-labile group is split as a consequence of a change in the pH value, this leads to a breaking up of the polyglycerol nanogel and thus to the release of an active substance contained in the nanogel, such as, for instance, a protein. The remains of the polyglycerol structure can then readily be degraded by an organism, as they are not toxic.

The term "pH-labile", hence, defines the property that at specific pH values (depending on the bond of the reactive groups) the previously formed covalent bonds split up and thereby a disintegration of the nanogels is caused. Reactive groups differ from the pH-labile groups in that their reactive stability is pH-independent. It is possible that the pH-labile groups form covalent bonds. These covalent bonds are then-unlike covalent bonds formed by non-pH-labile groups—pH-labile as desired, that is, cleavable depending on the pH value.

In an embodiment, the pH-labile group is selected from the group consisting of acetals, ketals, enol ethers, enol esters, amides of 2,3-disubstituted maleic acid derivatives, imines, iminium compounds, enamines, silyl ethers and silyl enol ethers.

Here, particularly acetals have turned out to be suitable pH-labile groups. Alkyl acetals or aryl acetals such as, for instance, the benzacetal, have turned out to be especially suitable pH-labile groups.

An especially suited and simple synthesis of the polyglycerol nanogel is possible when the pH-labile group is linked to the reactive group and together they are attached to the polyglycerol basic structure. Hence, in an embodiment, the first polyglycerol macromonomers and/or the second polyglycerol macromonomers have a terminal modification of the type —R—R', which is covalently bound to a linear or branched polyglycerol structure of the first polyglycerol macromonomers and/or of the second polyglycerol macromonomers. The polyglycerol basic structure here can also be referred to as "A", resulting in a schematic structure in the form of A-R—R'.

R here is a pH-labile group and R' a terminal group that can undergo a reaction according to click chemistry. In an embodiment, R' is a bioorthogonal group, which can then react with the bioorthogonal reactive groups of the respective other makromonomers when brought together in the non-solvent by means of click chemistry and form a covalent bond. The term click chemistry, generally known to a person skilled in the art, specifies chemical reactions which can be carried out bioorthogonally, chemoselectively and at high speed at roughly 100% conversion. Reactions according to click chemistry are configured modular and have a wide range of possible applications, high yields, and a high thermodynamic driving force. Moreover, practically no byproducts are formed. They are described, for instance, by Sharpless et al. (K. B. Sharpless et al. Angew. Chem. Int. Ed. Engl. 2001, 40, 2004-2021). Here, reactions according to click chemistry can take place, for example, catalyzed by copper, or else, without being catalyzed.

In an embodiment, the pH-labile bonds, introduced by the pH-labile groups R, have a high stability at a pH value of 7-8, particularly at a pH value of 7.2 to 7.8, particularly at a pH value of 7.4 to 7.6, that is, under the reaction conditions usually chosen. However, if acidic pH values are reached (pH 4-6, particularly pH 4.5-5.5, particularly pH 4.8-5.3), the pH-labile bond splits and the polymer network is degraded.

In an embodiment, a pH-labile group is integrated only into one type of macromonomers. By a subsequent linking of the first type of macromonomers to the second type of macromonomers, a correspondingly homogenous distribution of pH-labile groups over the entire polyglycerol nanogel is ensured.

Especially if additional substances are to be embedded in the nanogel also, particularly mild reaction conditions are suited. In an embodiment, the present method is, hence, carried out at a temperature of 0° C. to 25° C. Temperatures of 2° C. to 20° C., particularly of 3° C. to 15° C. and very particularly of 4° C. to 10° C. have turned out to be especially suitable reaction conditions. At such low temperatures, other known methods for producing polyglycerol nanogels do not take place with a sufficiently high reaction speed.

The click chemistry already mentioned previously can be carried out in an especially suited manner when a reaction between an alkyne and an azide takes place. Hence, in an embodiment, the first reactive group is an alkyne group and the second reactive group is an azide group (or vice versa). The first reactive group or the second reactive group corresponds to the group R' of one of the previously explained alternative embodiments of the method. Such alkyne groups that have one, two, three, four, five, six, seven, eight, nine or ten carbon atoms have turned out to be especially suitable alkyne groups, wherein linker with a terminal triple bond according to —$(CH_2)_n$—≡with n=1-10 or strained cyclical alkynes can be employed. These groups can here be connected via heteroatoms such as, for instance, oxygen, nitrogen or sulfur atoms to further modification groups or to the nucleus of the polyglycerol macromonomer. An especially suitable alkyne group is the propargyloxy group.

In order to ensure that the proteins or other active substances themselves do not participate in the cross-linking reaction between the first macromonomer and the second macromonomer and in order to thus prevent a possible denaturation of the proteins or of the other active substances, the method is executed as a bioorthogonal reaction in an embodiment. An especially suited reaction mechanism consists in the copper-catalyzed 2,3-cycloaddition of multifunctional polyglycerol alkynes and polyglycerol azides. In order to avoid copper contaminations, however, a catalyst-free cross-linking reaction of strained polyglycerol cyclooctynes with polyglycerol azides is also suitable. Further reactions are equally conceivable.

In a variant, the precipitation of the polyglycerol nanogel takes place without adding a compound containing copper. That is to say, the reaction environment, in which the precipitation reaction takes place, is in an embodiment completely free of copper. In particular, in the entire method no compound containing copper is employed. Surprisingly, it could be shown that a polyglycerol nanogel can be precipitated effectively even without using the toxic agent copper, wherein embedding biologically active substances is also possible in this case. This variant allows for an even gentler embedding of biologically active substances.

Also subject-matter of an aspect of the invention is a polyglycerol nanogel having at least one pH-labile group. Here, in an embodiment of the polyglycerol nanogel, the pH-labile groups explained in the context of explaining the possible embodiments of the method for producing a polyglycerol nanogel can be employed. Furthermore, the further alternative embodiments of the method are in an analogous manner also transferrable to the claimed polyglycerol nanogel.

Subject-matter of an aspect of the invention, moreover, is the use of such a polyglycerol nanogel as a carrier for a substance, for instance, for a peptide, a protein, a nucleic acid and/or a hormone. Further details of aspects of the present invention will be explained in more detail with the help of figures and exemplary embodiments.

BRIEF DESCRIPTION OF THE DRAWINGS

FIG. 1 shows a schematic illustration of an exemplary embodiment of a method for producing a polyglycerol nanogel;

FIG. 3 shows a schematic illustration of an exemplary embodiment of a method for producing a polyglycerol nanogel with the simultaneous embedding of a protein;

DETAILED DESCRIPTION

Figure 2A:
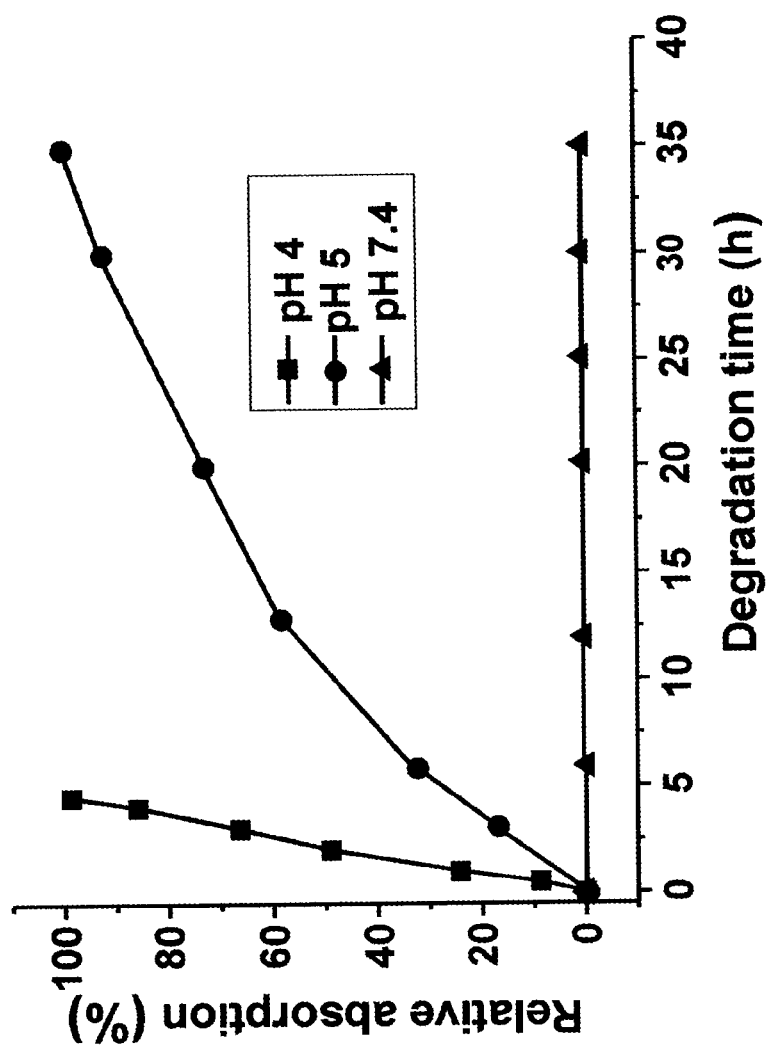
FIG. 2A shows a graphic illustration of the decomposition of a pH-labile polyglycerol nanogel at different pH values.

FIG. 1 shows a schematic illustration of a method for producing a polyglycerol nanogel. First polyglycerol macromonomers (1) are here mixed with second polyglycerol macromonomers (2) in low concentration. The first macromonomers carry in each case five propargyloxybenzacetal groups (10) as first reactive group or alkyne group. The second macromonomers carry in each case five azide groups (20) as second reactive groups or azide groups. The alkyne unit of the propargyloxybenzacetal groups (10) here is terminally located. This alkyne unit as such is stable. The azide groups (20) of the second macromonomers (2) are likewise terminally located. The mixture of first macromonomers (1) and second macromonomers (2) is present in an aqueous phase and is introduced into acetone (4) as organic non-solvent. Subsequently, there is a diffusion (5) of the water from the aqueous phase (3) into the acetone (4). Thereby, the concentration of the first macromonomers (1) and the second macromonomers (2) in the aqueous phase (3) increases. Thereby, the concentration of the macromonomers (1, 2) critical for initiating the reaction is reached, so that there is a reaction between the alkyne groups (10) and the azide groups (20). Covalent bonds form between the first macromonomers (1) and the second macromonomers (2), resulting in a formation of nanoparticles (6). In this manner, a polyglycerol nanogel 6 forms by swelling. This reaction, schematically illustrated in FIG. 1, will now be illustrated in more detail with the help of a specific exemplary embodiment.

Producing p-propargyloxy-benzaldehyde 2.00 g 4-hydroxybenzaldehyde (16.38 mmol) were dissolved in 50 ml acetone. 15.15 g potassium carbonate (109.62 mmol) were added, and the suspension was stirred for 30 minutes under reflux. After the solution had cooled down to room temperature, 2.12 ml propargylic bromide (19.10 mmol) were added over a period of 2.5 hours. Thereafter, the suspension was heated for 1.5 hours under reflux. The suspension was then filtered and the solvent of the filtrate was evaporated in vacuum. 50 ml dichloromethane were added and the organic phase thereafter was washed twice with 20 ml 1 M caustic soda and once with 20 ml water. The organic phase was dried over magnesium sulfate. The raw product was purified by means of Kugelrohr distillation. A white crystalline solid was obtained. As the results of an analysis show, the reaction was complete with a yield of about 80%.

Producing p-propargyloxy-benzdimethylacetal 1 g p-propargyloxy-benzaldehyde (6.29 mmol) was dissolved in 10 ml trimethyl orthoformate. Thereafter, 108 mg dry p-toluenesulfonic acid (0.629 mmol) were added. The reaction mixture was heated to 65° C. for one hour and thereafter quenched by adding 25 ml saturated sodium hydrogen carbonate solution. The mixture was extracted three times with, in each case, 25 ml ethyl acetate, and the fractions were merged and dried over sodium sulfate. The ethyl acetate was evaporated and p-propargyloxy-benzdimethylacetal was obtained as a yellowish oil at a yield of 90%.

Producing 3-azidopropyl 4-toluenesulphonate

In a two-necked flask, equipped with a dropping funnel and a stir bar, 3-azidopropanol (3.187 g, 31.52 mmol) and triethylamine (9.65 ml, 69.3 mmol, 2.2 molar equivalents (eq.)) were dissolved in dichloromethane (30 ml). After cooling down to 4° C. by means of an aqueous ice bath, a solution of tosyl chloride (6.61 g, 34.7 mmol, 1.1 eq.) in dichloromethane (30 ml) was added in drops within 10 min. The reaction was carried out further for 6 h at room temperature and the reaction process was monitored by IR-spectroscopy and thin-layer chromatography. After filtering out the formed salt, the filtrate was concentrated, taken up in dichloromethane (50 ml) and washed with a 1M $NH_4Cl$-solution (20 ml). The organic phase was dried over $MgSO_4$ and concentrated. The substance was ultimately purified by column chromatography on silica gel (hexane/ethyl acetate, 3:1) in order to obtain 3-azidopropyl 4-toluenesulphonate (6.44 g, 80%) as a yellow liquid. $R_f$: 0.64 (hexane/ethyl acetate, 3:1).

Producing 4-(3-azidopropoxy)-2-methoxybenzaldehyde $K_2CO_3$ (16.50 g, 119.5 mmol, 5 eq.) was added into a solution of 4-hydroxy-2-methoxybenzaldehyde (3.66 g, 23.9 mmol, 1.2 eq.) and 3-azidopropyl 4-toluenesulphonate (5.08 g, 19.91 mmol, 1 eq.) in acetone (70 ml). The reaction was carried out for 16 h under reflux and, after cooling down to room temperature, salt was filtered out and the filtrate was concentrated. After the uptake of the residue in dichloromethane (20 ml), the organic phase was washed with water (20 ml), dried over $MgSO_4$ and then concentrated. The substance was ultimately purified by column chromatography on silica gel (hexane/ethyl acetate, 3:1) in order to obtain 4-(3-azidopropoxy)-2-methoxybenzaldehyde (3.98 g, 85%) as a transparent liquid. $R_f$: 0.54 (hexane/ethyl acetate, 3:1).

Producing 4-(3-azidopropoxyl)benzaldehyde $K_2CO_3$ (13.55 g, 98.05 mmol, 5 eq.) was added into a solution of 4-hydroxybenzaldehyde (2.39 g, 19.61 mmol, 1.2 eq.) and 3-azidopropyl 4-toluenesulphonate (5.08 g, 19.91 mmol, 1 eq.) in acetone (70 ml). The reaction was carried out for 16 h under reflux and, after cooling down to room temperature, salt was filtered out and the filtrate was concentrated. After the uptake of the residue in dichloromethane (20 ml), the organic phase was washed with water (20 ml), dried over $MgSO_4$ and then concentrated. The substance was ultimately purified by column chromatography on silica gel (hexane/ethyl acetate, 2:1) in order to obtain 4-(3-azidopropoxyl)benzaldehyde (3.98 g, 91%) as transparent liquid. $R_f$: 0.67 (hexane/ethyl acetate, 2:1).

Producing 4-(3-azidopropoxy)-2-methoxybenzaldehyde-dimethylacetal

Trimethyl orthoformate (5.20 ml, 49.02 mmol, 5 eq.) and PTSA without water (169 mg, 0.98 mmol) were added into a solution of 4-azidopropoxy-2-methoxybenzaldehyde (2.00 g, 9.80 mmol) in degassed methanol (20 ml). The reaction was carried out for 20 h under reflux and, after cooling down, quenched with aqueous ammonia (0.5 ml). After concentrating the solution, ethyl acetate (50 ml) was added and the solution was washed with water (50 ml). After drying the organic phase over MgSO$_4$, the organic phase was concentrated in order to obtain 4-(3-azidopropoxy)-2-methoxybenzaldehyde dimethylacetal (2.32 g, 95%) as a yellow liquid. R$_f$: 0.84 (hexane/ethyl acetate, 3:1).

Producing 4-(3-azidopropoxyl)benzaldehyde dimethylacetal

Trimethyl orthoformate (4.64 ml, 43.72 mmol, 5 eq.) and PTSA without water (169 mg, 0.98 mmol) were added to a solution of 4-azidopropoxybenzaldehyde (2.00 g, 8.51 mmol) in degassed methanol (20 ml). The reaction was carried out for 20 h under reflux and, after cooling down, quenched with aqueous ammonia (0.5 ml). After concentrating the solution, ethyl acetate (50 ml) was added and the solution was washed with water (50 ml). After drying the organic phase over MgSO$_4$, the organic phase was concentrated in order to obtain 4-(3-azidopropoxy)-2-methoxybenzaldehyde dimethylacetal (2.38 g, 97%) as a yellow liquid. R$_f$: 0.57 (hexane/ethyl acetate, 4:1).

Producing hPG$_{7,7}$, which is functionalized with 7 p-azidopropoxy-methoxybenzacetal units (hPG$_{7,7}$-7-p-azidopropoxy-benzacetal)

1 g hPG$_{7,7}$ (0.13 mmol) and 365.3 mg of 4-(3-azidopropoxy)-2-methoxybenzaldehyde dimethylacetal (1.3 mmol) were dissolved in 4 ml n-methyl-2-pyrrolidone, and 22 mg p-toluenesulfonic acid without water (0.13 mmol) were added. The reaction mixture was held at room temperature for three hours and the condensed methanol was removed from the reaction mixture by cryo-distillation. The reaction was quenched by adding 1 ml aqueous ammonia. The n-methyl-2-pyrrolidone was evaporated by cryo-distillation, and the remaining residue was again dissolved in basified water (basified water contains 0.05 wt % aqueous ammonia). The solution was dialyzed in basified water for five days, wherein the dialysate was changed every three hours. After freeze-drying, hPG$_{7,7}$ functionalized with seven p-azidopropoxy-methoxybenzacetal units was obtained as a viscous wax. The reaction took place with a conversion of 71% and a yield of 78%.

Producing hPG$_{7,7}$, which is functionalized with 7 p-azidopropoxybenzacetal units (hPG$_{7,7}$-7-p-azidopropoxy-benzacetal)

1 g hPG$_{7,7}$ (0.13 mmol) and 326.3 mg of 4-(3-azidopropoxyl)benzaldehyde dimethylacetal (1.3 mmol) were dissolved in 4 ml n-methyl-2-pyrrolidone, and 22 mg p-toluenesulfonic acid without water (0.13 mmol) were added. The reaction mixture was held at room temperature for three hours and the condensed methanol was removed from the reaction mixture by cryo-distillation. The reaction was quenched by adding 1 ml aqueous ammonia. The n-methyl-2-pyrrolidone was evaporated by cryo-distillation, and the remaining residue was again dissolved in basified water (basified water contains 0.05 wt % aqueous ammonia). The solution was dialyzed in basified water for five days, wherein the dialysate was changed every three hours. After freeze-drying, hPG$_{7,7}$ functionalized with seven p-azidopropoxy-methoxybenzacetal units was obtained as a viscous wax. The reaction took place with a conversion of 69% and a yield of 83%.

Producing hPG7,7, which is functionalized with 7p-propargyloxy-benzacetal units (hPG$_{7,7}$-7-p-propargyloxy-benzacetal)

1 g hPG$_{7,7}$ (0.13 mmol) and 250 mg p-propargyloxy-benzdimethylacetal (1.3 mmol) were dissolved in 4 ml n-methyl-2-pyrrolidone, and 22 mg p-toluenesulfonic acid without water (0.13 mmol) were added. The reaction mixture was heated to 120° C. for three hours and the condensed methanol was removed from the reaction mixture by cryo-distillation. After cooling down to room temperature, the reaction was quenched by adding 1 ml aqueous ammonia. The n-methyl-2-pyrrolidone was evaporated by cryo-distillation, and the remaining residue was again dissolved in basified water (basified water contains 0.05 wt % aqueous ammonia). The solution was dialyzed in basified water for two hours, wherein the dialysate was changed every three hours. After freeze-drying, hPG$_{7,7}$ functionalized with seven p-propargyloxy-benzacetal units was obtained as a viscous wax. The reaction took place with a conversion of 70% and a yield of 80%.

Producing homobifunctional 1PG$_5$-biscyclooctyne

P(EEGE)$_5$-Br (4 g, 0.8 mmol) was dissolved in tetrahydrofuran (20 ml) and the solution was cooled down to 4° C. by means of an ice bath. After the addition of triethylamine (2.23 ml, 16 mmol) and mesyl chloride (0.62 ml, 8 mmol), the reaction was carried out for one day at room temperature. After salt filtration, the polymer was purified by means of dialysis in THF. Subsequently, the polymer (2 g, 0.4 mmol) was taken up in DMF (20 ml) and caused to react with NaN$_3$ (520 mg, 8 mmol) at 80° C. for three days, the salt was filtered out, the protective groups were deprotected by means of ethanolic HCL (1 vol. %) and then purified by means of a three-day dialysis. Thereafter, the azided polymer (1.8 g, 0.36 mmol) was reduced for three days in a water-THF mixture (10 ml, 1:1) by triphenylphosphine (377.3 mg, 1.44 mmol). The diamine formed (1 g, 0.2 mmol) was ultimately with BCN (138.6 mg, 0.44 mmol) in dichloromethane (10 ml) with triethylamine (0.88 mmol, 123 µL) as base. The polymer was processed by means of a three-day dialysis in a water-acetone mixture (1:1) in order to obtain 1PG$_5$-biscyclooctyne.

Producing a Polyglycerol Nanogel by Nanoprecipitation 5 mg hPG$_{7,7}$-7-p-propargyloxy-benzacetal (0.6 µmol) and 7 mg hPG$_{7,7}$[N$_3$]$_7$ (0.9 µmol) were dissolved in 0.5 ml purified deionized water, independently of one another. Tris(3-hydroxypropyltriazolylmethyl) (THPTA), copper sulfate and sodium ascorbate were added to the hPG$_{7,7}$-7-p-propargyloxy-benzacetal solution in precisely that order. The solutions were cooled down to 4° C. The solutions were then mixed with each other and quickly added to 20 ml acetone, which was stirred by a magnetic stirrer. This now led to the precipitation of polyglycerol nanoparticles, which were visible as bluish-appearing dispersions. The particle size was detected by means of dynamic light scattering (DLS). After three hours, the gel formation reaction was quenched by adding an excess of 50 mg azidoglycerol (427 µmol). After 12 hours, 20 ml purified deionized water were added, and the acetone was evaporated in order to obtain a bluish-shimmering nanogel dispersion in water. The nanogel was separated from the aqueous phase by centrifugation at 4000 rpm and washed five times with purified deionized water. The nanogel was thereafter characterized by means of DLS, optical microscopy and transmission electron microscopy.

Embedding Proteins, Including an L-Asparaginase II, a Bovine Serum Albumin, the Antibody IgG and a Lysozyme, in the Nanogel 2 mg hPG$_{7,7}$-7-p-propargyloxy-benzacetal (0.2 µmol) and 3 mg hPG$_{7,7}$[N$_3$]$_7$ (0.3 µmol) were dissolved in 0.5 ml purified deionized water, independently of one another. THPTA and copper acetate were added to the hPG$_{7,7}$-7-p-propargyloxy-benzacetal solution. Furthermore, the protein was added to the hPG$_{7,7}$[N$_3$]$_7$ solution. The solutions were cooled down to 4° C. Thereafter, the solutions were mixed and quickly added to 20 ml acetone, which was stirred on a magnetic stirrer. After three hours, the gel formation reaction was quenched by adding an excess of 50 mg azidoglycerol (427 µmol). After 12 hours, the nanogel was separated from the liquid phase by means of centrifugation at 4000 rpm and washed five times with purified deionized water.

Embedding Proteins, Including an L-Asparaginase II, a Bovine Serum Albumin, the Antibody IgG and a Lysozyme, in the Nanogel by Copper-Free Click Chemistry 2 mg $hPG_{7,7}$-7-p-azidopropoxy-benzacetal (0.2 µmol) and 4 mg $1PG_5$-biscyclooctyne (0.6 µmol) were dissolved in 0.5 ml purified deionized water, independently of one another. Furthermore, the protein was added to the $hPG_{7,7}$-7-p-azidopropoxy-benzacetal solution. The solutions were cooled down to 4° C. Thereafter, the solutions were mixed and quickly added to 20 ml acetone, which was stirred on a magnetic stirrer. After three hours, the gel formation reaction was quenched by adding an excess of 50 mg azidoglycerol (427 µmol). After 12 hours, the nanogel was separated from the liquid phase by means of centrifugation at 4000 rpm and washed five times with purified deionized water.

Determining the Size of the Nanogel Particles

As the subsequent Table 1 shows, the size of the polyglycerol nanogels obtained depends on the starting concentration of the macromonomers employed.

TABLE 1

Dependency of the size of the formed polyglycerol nanoparticles on the starting concentration of the macromonomers employed

| c (macromonomer)/ (mg/ml) | d/nm (in acetone) | PDI (in acetone) | d/nm (in water) | PDI (in water) |
| --- | --- | --- | --- | --- |
| 12 | 580 | 0.03 | 820 | 0.07 |
| 6 | 440 | 0.02 | 610 | 0.03 |
| 3 | 310 | 0.06 | 430 | 0.08 |
| 1.5 | 102 | 0.04 | 145 | 0.07 |

The lower the starting concentration of the macromonomers, the smaller the diameter of the nanogels formed. Here, in Table 1, c is the concentration, d the diameter and PDI the polydispersity. Whereas with a macromonomer concentration of 1.5 mg/ml, polyglycerol nanogels having a diameter of about 100 nm in acetone were obtained, this diameter increased to just under 600 nm at a starting concentration of 12 mg/ml macromonomers. After transferring the nanogels into water, there was a further swelling of the nanogels due to the integration of water molecules. Thereby, the measured diameter of the nanogels also increased.

Polydispersity is a measure for the scattering of the particle sizes and indicates that the nanogels have a very narrow size distribution. When the particles are transferred from acetone into water, the particle sizes increase. This suggests the swelling of the particles.

Determining the Nanogel Degradation Kinetics

Nanogel dispersions were incubated at 37° C. and at different pH values. After different times of incubation, the nanogels were cooled down to 4° C., neutralized and separated from degraded fragments by means of a 5-minute centrifugation at 4000 rpm. Thereafter, the UV-absorption of the degraded fragments located in the supernatant solution was observed at 350 nm. During the degradation, more and more degraded fragments go into solution, causing the absorption to rise. The corresponding result of this experiment is illustrated in FIG. 2A. One can see well that at a pH value of 7.4 the integrity of the polyglycerol nanoparticles is not affected. Rather, the nanoparticles remain stable at this pH value. Only when the pH value is lowered, there is a degradation of the polyglycerol nanoparticles, for then the benzacetal compound contained in the nanoparticles formed is broken up. As is evident from FIG. 2A, the degradation of the polyglycerol nanoparticles furnished with the benzacetal groups goes faster, the lower the set pH value. At a pH value of 4, the polyglycerol nanoparticles are completely degraded in less than five hours.

The complete nanogel degradation was confirmed by means of DLS-size measurements and $^1$H-NMR-spectroscopic measurements.

Controlled Release of Asparaginase Initiated by pH-Dependent Nanogel Degradation The polyglycerol nanogel loaded with L-asparaginase II according to the protocol explained above (10 mg/ml nanogel and 0.5 mg/ml L-asparaginase II) was acidified with hydrochloric acid to pH 4 or pH 5, respectively. The samples were incubated at room temperature (25±2° C.) under a slight motion (300 rpm). Individual samples were collected over the course of three days and, thereafter, analyzed by means of size exclusion high-performance chromatography (SEC-HPLC). In order to stop the nanogel degradation, the samples were neutralized with 0.1 M caustic potash prior to the SEC-HPLC. For the SEC-HPLC, 50 µl of the neutralized samples were injected into a HPLC equipped with a TSKgel G40000 PWXL column (300×7.8 mm, 10 µm particle size). An isocratic elution with a buffer of 20 mM NaHPO4, 150 mM NaCl and 0.003 mM NaN3 (pH 7.4) at a flow rate of 0.4 ml/min took place. The concentration of the L-asparaginase II was determined by means of UV-absorption at 280 nm and fluorescence detection (excitation with 295 nm and emission at 348 nm).

Figure 2B:
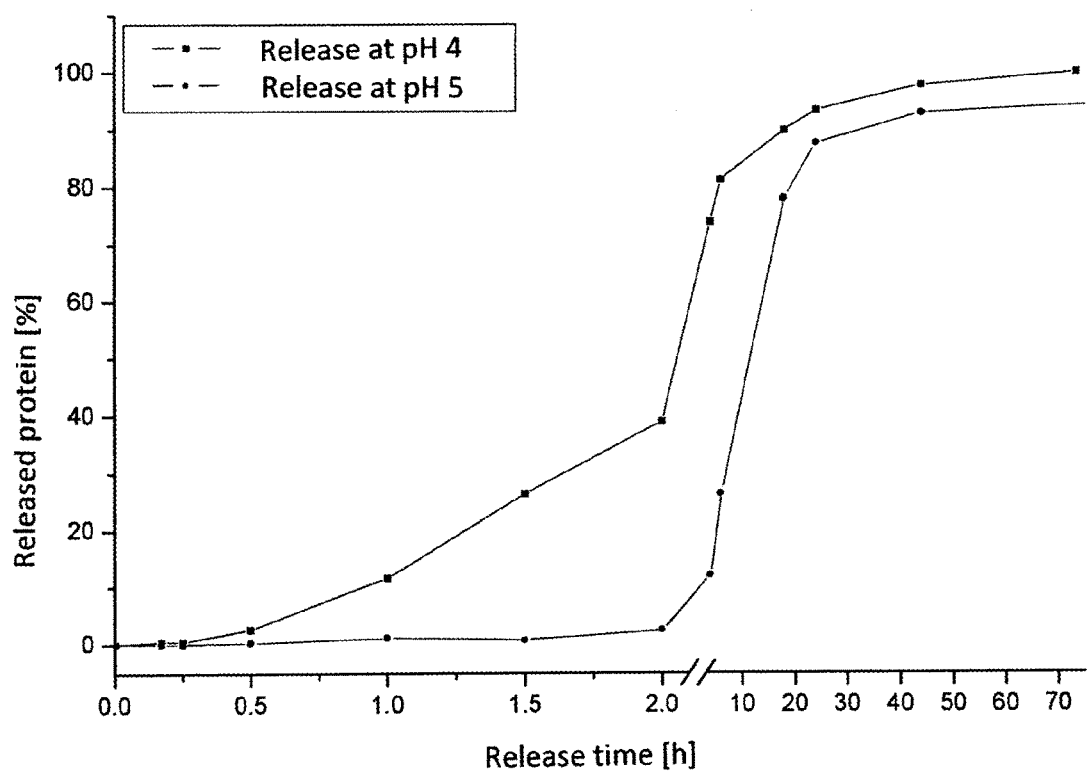
FIG. 2B shows a graphic illustration of the L-asparaginase-II release from a pH-labile polyglycerol nanogel at different pH values.

FIG. 2B shows the corresponding results of this examination. The obtained HPLC-chromatograms show that L-asparaginase II can be detected by means of the intrinsic tryptophan fluorescence without being impaired by polyglycerol or polyglycerol fragments. In the intact polyglycerol nanogel loaded with L-asparaginase II, no free L-asparaginase could be detected. Hence, the loading or embedding efficiency was at roughly 100%. By means of the chromatograms the percentage of the released L-asparaginase II was determined and plotted against time in FIG. 2B. As expected, the L-asparaginase II was released faster at pH 4 (square data points) than at pH 5 (round data points), since at a lower pH value, a faster nanogel degradation takes place.

FIG. 3 shows a schematic illustration of the previously explained embedding of a protein 7 in the formed nanoparticles or the formed nanogel 6. A joint nanoprecipitation of polyglycerol macromonomers and a protein leads to an in situ gel formation, wherein the also precipitated proteins are embedded inside of the nanogel in their native form. When the protein-loaded polyglycerol nanogel 8 is transferred into an acidic medium, it comes to the degradation and protein release 9. One can make use of this fact, because low pH values predominate in inflamed or tumor tissue of an organism. In this manner it is possible to place a nanogel loaded with a therapeutic protein into an organism, wherein the therapeutic protein is released only at its site of action (namely the inflamed tissue with a low pH value). Instead of embedding or integration, one can also speak of the encapsulation of a protein or of another active substance.

As already mentioned, harsh reaction conditions are not suited to maintain a protein or another labile substance in its native and active form. In order to prove that proteins in the native form can be embedded in the formed nanogel with the method presently introduced, the secondary structure of L-asparaginase II, as an exemplarily embedded enzyme, was detected after encapsulation in and release from the nanogel. This was done by means of the Fourier transformation infrared spectroscopy (FTIR), wherein measuring was done in the form of attenuated total reflection measurements (ATR). The employed ATR cell was held at a constant temperature of 25° C. 25 µl of a sample were given onto the ATR cell under dry nitrogen and measured against PBS buffer with a pH value of 5 or against water as control. 120 scans for each experiment at a resolution of 4 cm$^{-1}$ were carried out, wherein a water vapor correction took place. The second derivatives of the obtained absorption spectra were used for further data analysis.

Figure 4A:
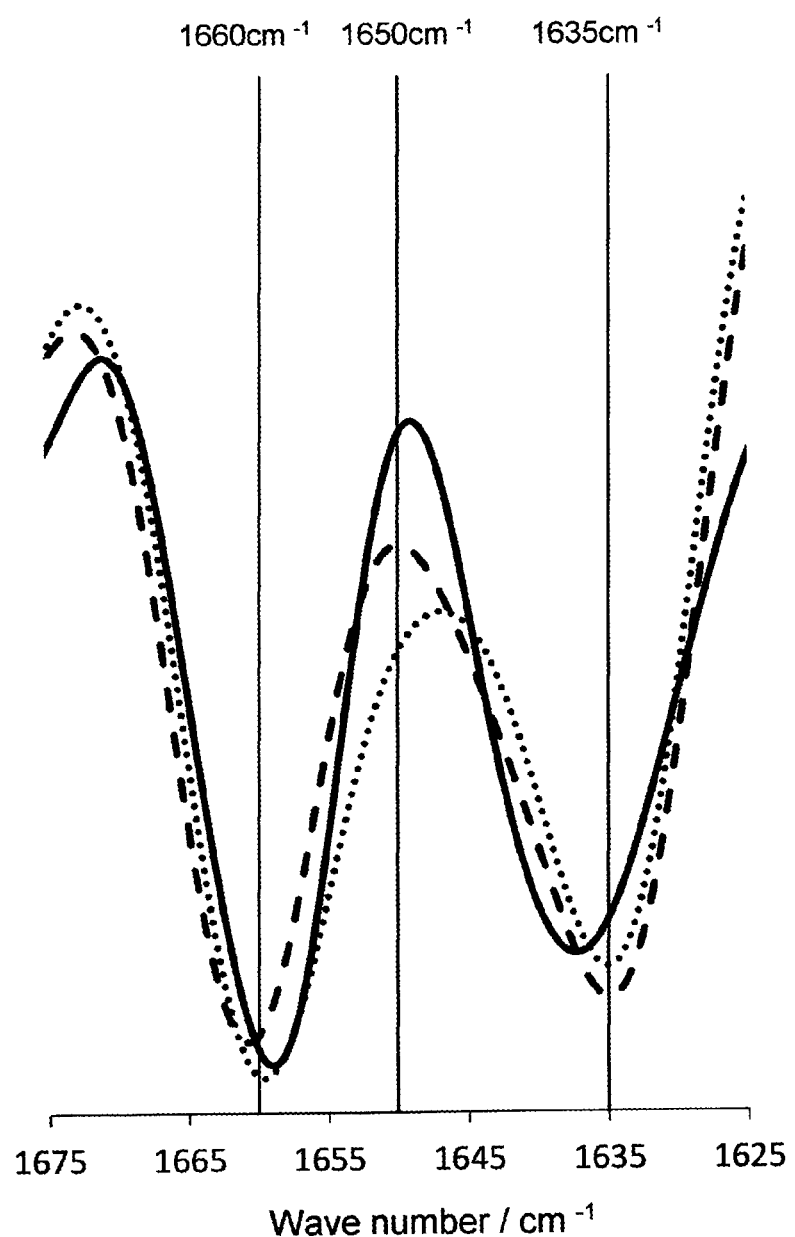
FIG. 4A shows second derivatives of absorption spectra of the model protein L-asparaginase II in the amide-I region after encapsulation and degradation of the nanogels.
Figure 4B:
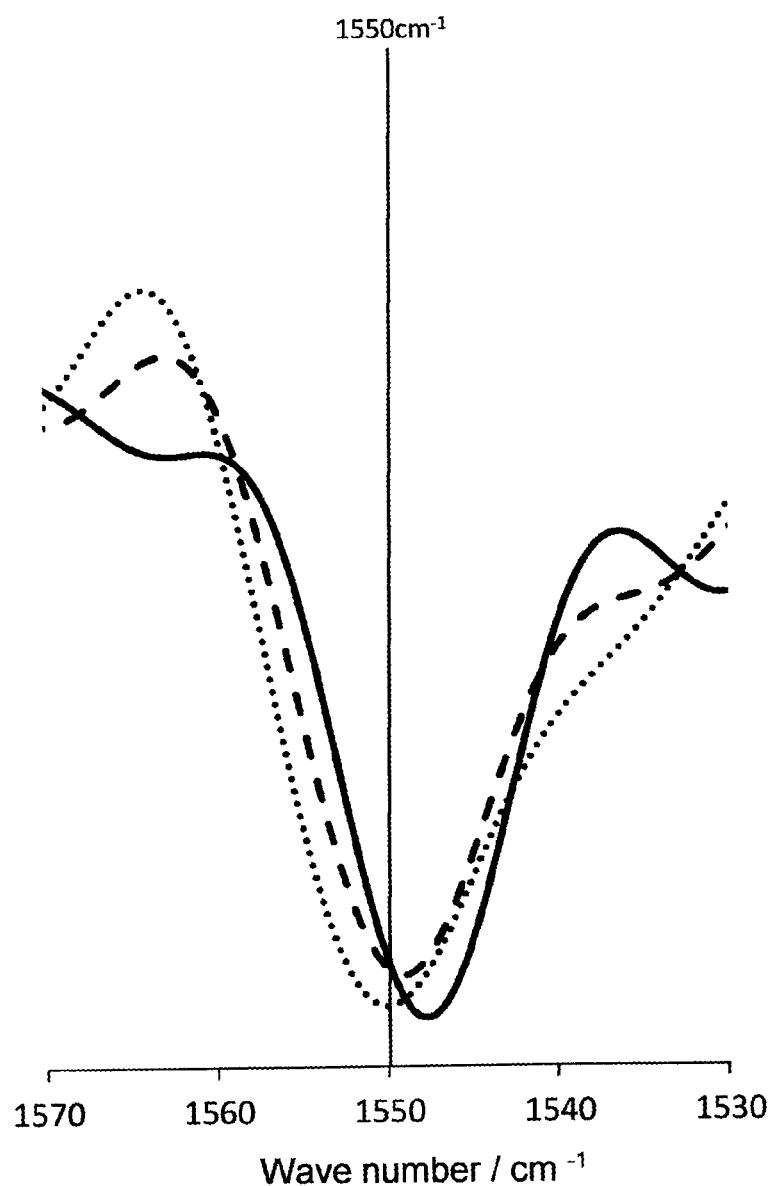
FIG. 4B shows second derivatives of absorption spectra of the model protein L-asparaginase II in the amide-II region after encapsulation and degradation of the nanogels.

The result of these FTIR-examinations is illustrated in FIGS. 4A and 4B. Here, FIG. 4A shows absorptions observed in the region of the amide-I band, whereas absorptions in the region of the amide-II band are illustrated in FIG. 4B. The amid-I band is sensitive to C=O stretching vibrations and is well suited to determine the secondary structure of a protein.

The second derivative of the spectrum of native L-asparaginase II dissolved in water (freshly prepared) is illustrated as a dashed line in FIGS. 4A and 4B. The dotted line shows the second derivative of an absorption spectrum of L-asparaginase II which was stored for seven days in PBS buffer at a pH value of 5. The continuous line finally shows the second derivative of an absorption spectrum of L-asparaginase II released from polyglycerol nanogels after seven days.

As can be seen from FIG. 4A, neither the band intensities nor the wave numbers of the three different samples differ from each other significantly. Rather, merely a slight shift of the band characteristic for a α-helical secondary structure at 1660 cm$^{-1}$ by 1 cm$^{-1}$ to lower wave numbers can be observed. With the band characteristic for a β-sheet secondary structure at approximately 1635 cm$^{-1}$ for the native protein, no shift can be observed. Altogether, however, these shifts lie within the range of error due to the measuring technique. Thus, it is to be assumed that the secondary structure is not changed by an encapsulation of the L-asparaginase II in the polyglycerol nanoparticles.

This finding is also confirmed by an analysis of the amide-II band. The amide-II band provides information about the N—H bending vibrations and the C—N stretching vibrations. Herein, when storing the L-asparaginase II in water or encapsulating this enzyme in the polyglycerol nanogels, likewise no significant band shift (see FIG. 4B) can be detected.

The observed absorptions in the amide-I and amide-II region are illustrated in the subsequent Table 2.

TABLE 2

Absorptions of the L-asparaginase in the amide-I and amide-II region, determined with the help of the second derivatives of corresponding absorption spectra

|  | Absorptions in the region of the amide-I band/cm$^{-1}$ | | Absorptions in the region of the amide-II band/cm$^{-1}$ |
| --- | --- | --- | --- |
| L-asparaginase II in water (freshly prepared) | 1660.5 | 1634.4 | 1549.6 |
| L-asparaginase II in PBS pH 5.0 (7 d storage) | 1659.5 | 1635.4 | 1550.5 |
| L-asparaginase II after release (7 d storage) | 1659.0 | 1637.3 | 1547.6 |

Determining the Asparaginase Activity

The activity of the L-asparaginase II was determined by means of Neβler's ammonia quantification.

In order to carry out the asparaginase activity tests, 50 µl L-asparaginase II, 100 µl Tris-HCl with a pH value of 8.6 and 850 µl L-asparagine monohydrate buffer solution were incubated at 37° C. for 10 minutes. After the addition of 50 µl of a 1.5 M solution of trichloroacetic acid and subsequent centrifugation, 100 µl of the supernatant were added to Neβler's reagent. After 10 minutes, the optical density at 436 nm was determined and compared to a calibration curve as well as corrected by the total enzyme content. Calculating the enzyme activity then took place according to the following formula:

$$U/mg = \frac{\mu mol\ released\ ammonia}{10\ min \times mg\ enzyme\ in\ the\ reaction}$$

A unit (1 U) of the detected enzyme activity here corresponds to the released amount of ammonia in micromol per 10 minutes from asparagine as substrate.

The result of this quantification showed an activity of the freshly prepared asparaginase solution of 98.6 U/mg, which coincides with the data specified by the manufacturer (98.2 U/mg). When transferring L-asparaginase II into a PBS buffer with pH 5.0, the activity decreased by 10% to 86.1 U/mg. Storing the L-asparaginase II in the buffer over 7 days, reduces the activity by another 2.5% to 86.2 U/mg. An identical value, within the limits of measurement accuracy, could be detected for the activity of the L-asparaginase II which was encapsulated in a polyglycerol nanogel and released again, after its release. The measurement results are illustrated in the subsequent Table 3, together with the respectively detected standard deviations (SD).

TABLE 3

Enzyme activity of the L-asparaginase II

|  | Specific activity/ (U/mg) | Specific activity/ % | SD/ (U/mg) | SD/ % |
| --- | --- | --- | --- | --- |
| L-asparaginase II in water (freshly prepared) | 98.6 | 100 | 4.4 | 4.4 |
| L-asparaginase II in PBS pH 5.0 (freshly prepared) | 89.1 | 90.8 | 0.1 | 0.1 |
| L-asparaginase II in PBS pH 5.0 (7 d storage) | 86.1 | 87.3 | 0.7 | 0.8 |
| L-asparaginase II after release (7 d storage) | 86.2 | 87.5 | 0.9 | 1 |

Figure 5:
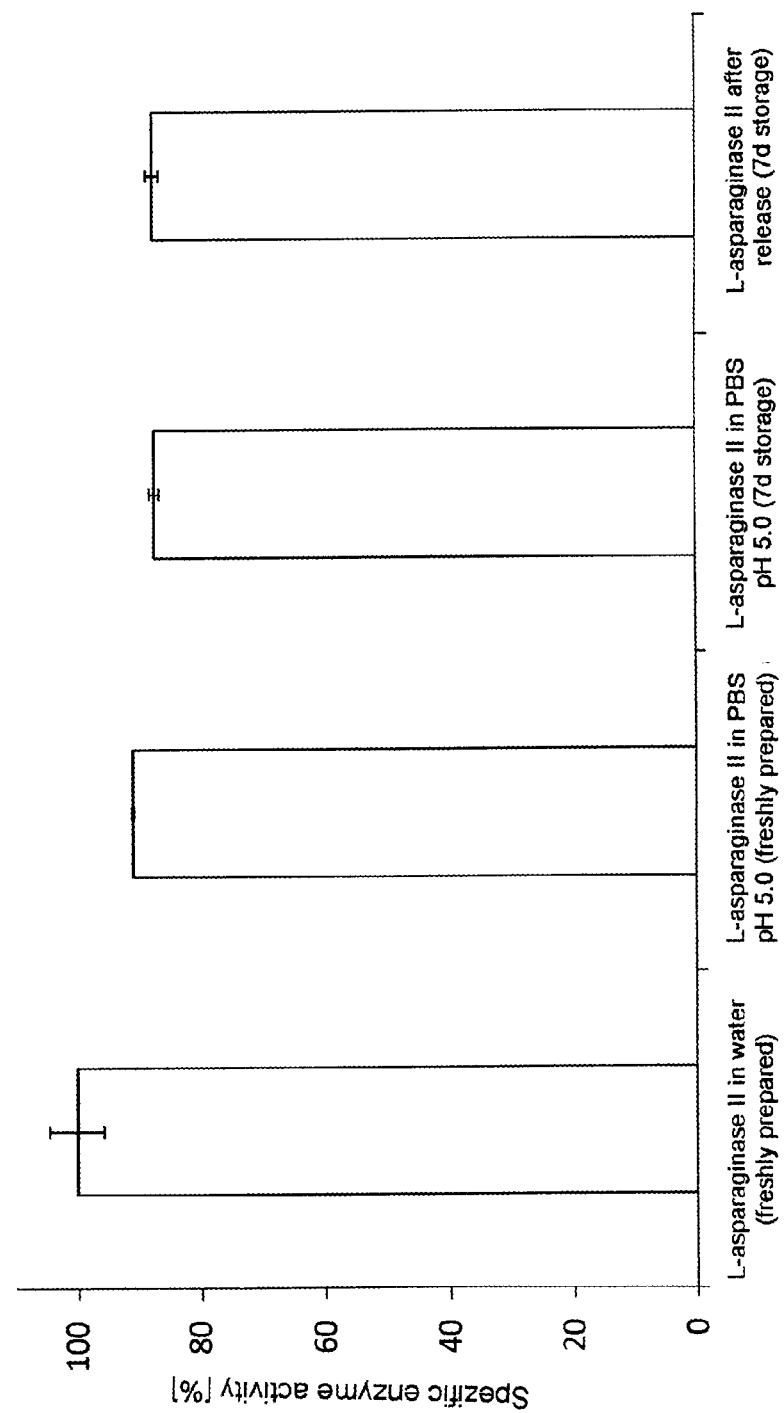
FIG. 5 shows a graphic illustration of the enzyme activity of the model protein L-asparaginase II after encapsulation and release from the nanogels and FIG. 6 shows a flow chart to illustrate the individual steps of the method of an exemplary embodiment.

A corresponding graphic illustration of the specific enzyme activity can be seen in FIG. 5. Here, the enzyme activity of the freshly prepared native L-asparaginase II in water was set to 100%. It is also evident from this graphic illustration that the L-asparaginase II, encapsulated in a polyglycerol nanogel, has an activity after its release that corresponds to the activity of L-asparaginase II dissolved in buffer. This confirms the results established by the FTIR-measurements. So, L-asparaginase II maintains its native secondary structure even after encapsulation in a polyglycerol nanogel. Furthermore, an encapsulation of L-asparaginase II in polyglycerol nanogels does not reduce the enzyme activity.

Figure 6:
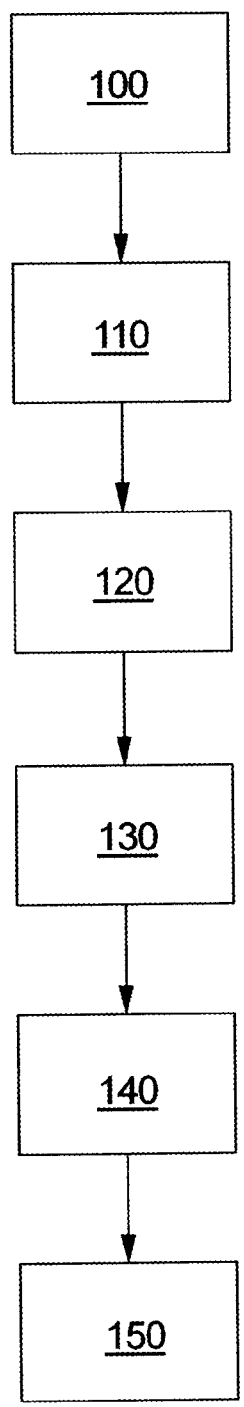

FIG. 6 shows a flow chart, which serves to illustrate an exemplary embodiment of the method claimed.

In a step 100 preceding the actual method itself, a synthesis of first polyglycerol macromonomers and of second polyglycerol macromonomers takes place.

In a first step of the process 110, an active merging of the first and the second polyglycerol macromonomers, a labile substance (a protein or enzyme, for instance) and, if required, a catalyst, which catalyzes the click reaction taking place later, takes place.

In a second step of the process 120, an active transferring of the merged substances into an organic non-solvent takes place. "Active" here means that an operator executes the corresponding steps by his or her willful actions.

In a third step of the process 130, there are two spontaneous chemical reactions, so that one can also speak of a double spontaneity. On the one hand, a spontaneous precipitation of the merged substances takes place with the spontaneous formation of nano-aggregates. On the other hand, a spontaneous cross-linking of the nano-aggregates takes place by a click reaction (forming covalent bonds between the first polyglycerol macromonomers and the second polyglycerol macromonomers).

Afterwards, the cross-linked nanoparticles are actively transferred into an aqueous phase in a forth step of the process 140.

Thereafter, in a fifth step of the process 150, a spontaneous swelling of the cross-linked particles takes place in aqueous phase.

The invention claimed is:

1. A method for producing a polyglycerol nanogel, comprising the following steps:
    mixing an aqueous solution of first polyglycerol macromonomers, which are modified with a first reactive group, with an aqueous solution of second polyglycerol macromonomers, which are modified with a second reactive group, wherein the first reactive group and the second reactive group can react with each other forming a covalent bond,
    transferring the mixture of both aqueous solutions into an organic non-solvent being miscible with water, allowing diffusion of water from the aqueous solutions into the organic non-solvent, thereby increasing the concentration of the first polyglycerol macromonomers and the second polyglycerol macromonomers,
    precipitation of a hydrophilic polyglycerol nanogel consisting of first polyglycerol macromonomers and second polyglycerol macromonomers which are covalently bound to each other, wherein the covalent bond between the first polyglycerol macromonomers and the second polyglycerol macromonomers is established by a reaction of the first reactive group and the second reactive group, which takes place spontaneously only as a consequence of transferring the mixture of both aqueous solutions into the organic non-solvent and increasing the concentration of the first polyglycerol macromonomers and the second polyglycerol macromonomers in the aqueous solutions,
    wherein the method is carried out at a temperature of between 0° C. to 25° C. without adding a surface-active substance.

2. The method according to claim 1, wherein method is carried out without using ultrasound.

3. The method according to claim 1, wherein the first polyglycerol macromonomers are present in a first concentration and the second polyglycerol macromonomers are present in a second concentration, wherein the first and the second concentration lie in a range of 0.1 to 30 mg/ml independently of each other.

4. The method according to claim 1, wherein the polyglycerol nanogel is transferred into an aqueous phase after precipitation.

5. The method according to claim 1, wherein the precipitation is carried out in the presence of a labile substance.

6. The method according to claim 1, wherein the first polyglycerol macromonomers and/or the second polyglycerol macromonomers contain a pH-labile group, which is still present in the polyglycerol nanogel formed.

7. The method according to claim 6, wherein the pH-labile group is selected from the group consisting of acetals, ketals, enol ethers, esters, amides, hydrazones, hydrazides, oximes, maleic acid derivatives, carbamates, hydroxylamine imines, iminium compounds, enamines, silyl ethers and silyl enol ethers.

8. The method according to claim 1, wherein the first polyglycerol macromonomers and/or the second polyglycerol macromonomers have a terminal modification of the type —R—R', which is covalently bound to a linear or branched polyglycerol structure of the first polyglycerol macromonomers and/or of the second polyglycerol macromonomers, wherein R is a pH-labile group and R' is a bioorthogonal terminal group that can undergo a reaction according to click chemistry.

9. The method according to claim 1, wherein the first reactive group is an alkyne group and the second reactive group is an azide group.

10. The method according to claim 1, wherein the precipitation of the polyglycerol nanogel takes place without adding a compound containing copper.

11. The method according to claim 5, wherein the labile substance is a peptide, a protein, DNA, RNA and/or a hormone.

12. The method according to claim 1, wherein the precipitation is carried out in the presence of a biologically active substance.

* * * * *